United States Patent
Fricker

(10) Patent No.: US 12,111,223 B2
(45) Date of Patent: Oct. 8, 2024

(54) DEVICE AND METHOD FOR EVALUATING A PERFORMANCE OF A VISUAL EQUIPMENT FOR A VISUAL TASK

(71) Applicant: ESSILOR INTERNATIONAL, Charenton-le-Pont (FR)

(72) Inventor: Sébastien Fricker, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 439 days.

(21) Appl. No.: 17/441,493

(22) PCT Filed: Mar. 20, 2020

(86) PCT No.: PCT/EP2020/057878
§ 371 (c)(1),
(2) Date: Sep. 21, 2021

(87) PCT Pub. No.: WO2020/193436
PCT Pub. Date: Oct. 1, 2020

(65) Prior Publication Data
US 2022/0146372 A1 May 12, 2022

(30) Foreign Application Priority Data

Mar. 22, 2019 (EP) .................... 19305359

(51) Int. Cl.
*G01M 11/02* (2006.01)
*A61B 3/00* (2006.01)
(Continued)

(52) U.S. Cl.
CPC ....... *G01M 11/0264* (2013.01); *A61B 3/0025* (2013.01); *A61B 3/0033* (2013.01); *A61B 3/113* (2013.01); *G06F 3/012* (2013.01)

(58) Field of Classification Search
CPC .. A61B 3/0025; A61B 3/113; G01M 11/0264; G06F 3/012
See application file for complete search history.

(56) References Cited

U.S. PATENT DOCUMENTS 6,499,843 B1    12/2002   Cox et al.
9,939,658 B1 *   4/2018   Gutierrez ................ G02C 7/04
(Continued)

FOREIGN PATENT DOCUMENTS

CN   105705982 A   6/2016
CN   106461983 A   2/2017
(Continued)

OTHER PUBLICATIONS

Office Action issued in Korean Patent Application No. 10-2021-7030008 dated Aug. 25, 2023.
(Continued)

*Primary Examiner* — Vincent H Tran
(74) *Attorney, Agent, or Firm* — NIXON & VANDERHYE

(57) ABSTRACT

This device for evaluating a performance of a visual equipment for at least one wearer of that equipment to perform at least one visual task includes: at least one input adapted to obtain a model of a scene where the task is performed, a model of the task including a sequence of points to be looked at, a model of the wearer including a movable head and at least one rotationally movable eye; at least one processor configured for determining a head posture for at least one of the points so that the model of the wearer looks respectively at that point, determining at least one task-directed performance parameter for the wearer performing the task with the head posture for that point, on the basis of the wearer, scene
(Continued)

and task models, providing the task-directed performance parameter for determining to which extent the equipment is appropriate for the wearer.

20 Claims, 4 Drawing Sheets

(51) Int. Cl.
*A61B 3/113* (2006.01)
*G06F 3/01* (2006.01)

(56) References Cited

U.S. PATENT DOCUMENTS

| | | | |
|---|---|---|---|
| 2009/0228810 A1 | 9/2009 | Shinohara et al. | |
| 2010/0110373 A1* | 5/2010 | Drobe | G02C 7/027 351/204 |
| 2013/0083288 A1* | 4/2013 | Shinohara | G02C 7/024 351/159.42 |
| 2015/0309338 A1* | 10/2015 | Chauveau | G02C 7/027 351/204 |
| 2016/0011437 A1* | 1/2016 | Nishimura | A61B 3/152 351/204 |
| 2016/0327813 A1 | 11/2016 | Baranton et al. | |
| 2017/0036111 A1* | 2/2017 | Shigeta | G01C 21/1656 |
| 2017/0090220 A1 | 3/2017 | Bonnin et al. | |
| 2017/0322430 A1* | 11/2017 | Fayolle | G02C 13/005 |
| 2018/0299696 A1 | 10/2018 | Heslouis | |
| 2019/0113770 A1 | 4/2019 | Tranvouez-bernardin | |
| 2019/0204620 A1* | 7/2019 | Bonnin | G02C 7/061 |
| 2019/0246095 A1 | 8/2019 | Kishimoto | |
| 2019/0278108 A1* | 9/2019 | Ang | G02C 7/025 |
| 2020/0146546 A1* | 5/2020 | Chene | A61B 3/0008 |
| 2022/0083134 A1* | 3/2022 | Kassner | G06F 3/013 |

FOREIGN PATENT DOCUMENTS

| | | | | |
|---|---|---|---|---|
| CN | 107645921 A | * | 1/2018 | ........... A61B 3/0008 |
| CN | 108139603 A | | 6/2018 | |
| CN | 108474970 A | | 8/2018 | |
| JP | 2009238204 A | | 10/2009 | |
| JP | 2015079127 A | | 4/2015 | |
| JP | 2016539363 A | | 12/2016 | |
| KR | 20030029999 A | | 4/2003 | |
| WO | 2017/064065 | | 4/2017 | |
| WO | 2017/157760 | | 9/2017 | |
| WO | 2018074528 A1 | | 4/2018 | |

OTHER PUBLICATIONS

International Search Report for PCT/EP2020/057878 dated May 20, 2020, 4 pages.
Written Opinion of the ISA for PCT/EP2020/057878 dated May 20, 2020, 8 pages.
Office Action issued in Japanese Patent Application No. 2021-556802 dated Sep. 4, 2023.
Office Action, issued in Chinese Patent Application No. 202080023005.X dated Nov. 23, 2023.

* cited by examiner

DEVICE AND METHOD FOR EVALUATING A PERFORMANCE OF A VISUAL EQUIPMENT FOR A VISUAL TASK

This application is the U.S. national phase of International Application No. PCT/EP2020/057878 filed Mar. 20, 2020 which designated the U.S. and claims priority to EP Patent Application No. 19305359.2 filed Mar. 22, 2019, the entire contents of each of which are hereby incorporated by reference.

FIELD OF THE INVENTION

The present invention relates to a device and method for evaluating a performance of a visual equipment for at least one wearer of that visual equipment to perform at least one visual task.

BACKGROUND OF THE INVENTION

Nowadays, the performance of a visual equipment such as an ophthalmic lens or a solar lens may be evaluated by using a number of criteria, namely, sharpness of vision, distortions or other criteria, for example related to binocular vision.

Evaluating sharpness of vision usually consists in evaluating the amount of aberrations such as power errors, residual astigmatism or higher order aberrations, for a given gaze direction toward an object point.

Evaluating distortions usually consists in evaluating the distortions of space for a given gaze direction and a given peripheral direction, related to the prismatic deviations of the lens.

Evaluating prismatic deviations of a lens may give some indications about the effect of those prismatic deviations on the posture or gaze direction of the wearer. However, such an approach is limited. Indeed, it does not provide direct information about a wearer's posture or gaze direction when that wearer is performing a visual task. The actual posture and gaze direction of the wearer actually result from a compromise between visual acuity and global comfort.

Moreover, the evaluation of a performance of a visual equipment generally results from lengthy and expensive test procedures which are carried out with real persons. In addition, such test results cannot be reused for wearers who significantly differ from those wearers who were involved in the tests.

Thus, there is a need for a more rapid and economic way of evaluating a performance of a visual equipment for a wearer to carry out one or more given visual tasks, where the performance evaluation may easily be reused for a predetermined group of wearers.

SUMMARY OF THE INVENTION

An object of the invention is to overcome the above-mentioned drawbacks of the prior art.

To that end, the invention provides a device for evaluating a performance of a visual equipment for at least one wearer of that visual equipment to perform at least one visual task, wherein it comprises:
at least one input adapted to:
  obtain a model of a scene where the at least one visual task is performed;
  obtain a model of the at least one visual task, the model of the at least one visual task comprising a sequence of points to be looked at in the model of the scene;
  obtain a model of the wearer, the model of the wearer comprising a head movable with respect to the model of the scene and at least one eye rotationally movable with respect to the head, the visual equipment cooperating with the at least one eye;
at least one processor configured for:
  determining at least one head posture for respectively at least one of the points so that the model of the wearer looks respectively at the at least one of the points;
  determining at least one task-directed performance parameter for the wearer performing the at least one visual task with the at least one head posture for respectively the at least one of the points, on the basis of the wearer model, the scene model and the visual task model;
providing the at least one task-directed performance parameter for determining to which extent the visual equipment is appropriate for the wearer.

Therefore, the device according to the disclosure makes it possible to use in particular a virtual model of the wearer to automatically determine head postures and evaluate a performance of a visual equipment in a potentially efficient and economic manner.

This makes it possible to determine a most appropriate visual equipment for the wearer to perform the considered visual task(s), for example by comparing two visual equipments in terms of their impact on the task-directed performance parameters associated with the wearer performing the considered visual task(s).

In addition, this makes it possible to personalize a lens for a given wearer, by further taking account of parameters of the given wearer such as prescriptions, half-pupillary distances, wearing conditions, characteristics of the scene being looked at and/or the nature of the visual task.

Moreover, the performance evaluation made by the device according to the disclosure may be applied to a given wearer population, thus avoiding the burden of repeating tests on various individuals.

The invention also provides a method for evaluating a performance of a visual equipment for at least one wearer of that visual equipment to perform at least one visual task, wherein it comprises:
  obtaining a model of a scene where the at least one visual task is performed;
  obtaining a model of the at least one visual task, the model of the at least one visual task comprising a sequence of points to be looked at in the model of the scene;
  obtaining a model of the wearer, the model of the wearer comprising a head movable with respect to the model of the scene and at least one eye rotationally movable with respect to the head, the visual equipment cooperating with the at least one eye;
  determining by at least one processor at least one head posture for respectively at least one of the points so that the model of the wearer looks respectively at the at least one of the points;
  determining by at least one processor at least one task-directed performance parameter for the wearer performing the at least one visual task with the at least one head posture, on the basis of the wearer model, the scene model and the visual task model;
  providing the at least one task-directed performance parameter for determining to which extent the visual equipment is appropriate for the wearer.

In particular modes, that method for evaluating is executed by the device for evaluating according to the disclosure, in any of its embodiments.

The invention further provides a computer program product for evaluating a performance of a visual equipment for at least one wearer of that visual equipment to perform at least one visual task, wherein it comprises one or more sequences of instructions that are accessible to a processor and that, when executed by that processor, cause that processor to:

obtain a model of a scene where the at least one visual task is performed;

obtain a model of the at least one visual task, the model of the at least one visual task comprising a sequence of points to be looked at in the model of the scene;

obtain a model of the wearer, the model of the wearer comprising a head movable with respect to the model of the scene and at least one eye rotationally movable with respect to the head, the visual equipment cooperating with the at least one eye;

determine at least one head posture for respectively at least one of the points so that the model of the wearer looks respectively at the at least one of the points;

determine at least one task-directed performance parameter for the wearer performing the at least one visual task with the at least one head posture for respectively the at least one of the points, on the basis of the wearer model, the scene model and the visual task model;

provide the task-directed performance parameter for determining to which extent the visual equipment is appropriate for the wearer.

As advantages of the method and the computer program product are similar to those of the device, they are not repeated here.

The computer program product is advantageously configured for executing the method in any of its execution modes.

BRIEF DESCRIPTION OF THE DRAWINGS

For a more complete understanding of the description provided herein and the advantages thereof, reference is now made to the brief descriptions below, taken in connection with the accompanying drawings and detailed description, wherein like reference numerals represent like parts.

DETAILED DESCRIPTION OF EMBODIMENTS

Figure 1:
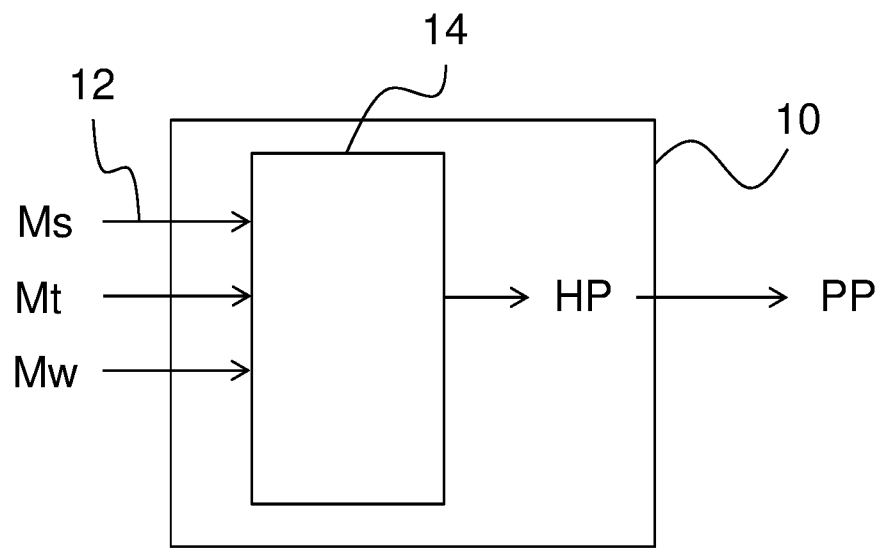
FIG. 1 is a schematic view of a device according to the invention, in a particular embodiment.

In the description which follows, the drawing figures are not necessarily to scale and certain features may be shown in generalized or schematic form in the interest of clarity and conciseness or for informational purposes. In addition, although making and using various embodiments are discussed in detail below, it should be appreciated that as described herein are provided many inventive concepts that may embodied in a wide variety of contexts. Embodiments discussed herein are merely representative and do not limit the scope of the invention. It will also be obvious to one skilled in the art that all the technical features that are defined relative to a process can be transposed, individually or in combination, to a device and conversely, all the technical features relative to a device can be transposed, individually or in combination, to a process.

The terms "comprise" (and any grammatical variation thereof, such as "comprises" and "comprising"), "have" (and any grammatical variation thereof, such as "has" and "having"), "contain" (and any grammatical variation thereof, such as "contains" and "containing"), and "include" (and any grammatical variation thereof such as "includes" and "including") are open-ended linking verbs. They are used to specify the presence of stated features, integers, steps or components or groups thereof, but do not preclude the presence or addition of one or more other features, integers, steps or components or groups thereof. As a result, a method, or a step in a method, that "comprises", "has", "contains", or "includes" one or more steps or elements possesses those one or more steps or elements, but is not limited to possessing only those one or more steps or elements.

As shown in FIG. 1, in a particular embodiment, a device 10 for evaluating a performance of a visual equipment for at least one wearer of that visual equipment to perform at least one visual task comprises one or more inputs 12 adapted to obtain a model Ms of a scene where the visual task is performed, a model Mt of the visual task and a model Mw of the wearer.

The visual equipment may be an ophthalmic lens or pair of ophthalmic lenses, or a solar lens or pair of solar lenses, or an ophthalmic solar lens or pair of ophthalmic solar lenses. It may be in the form of glasses or contact lenses. The visual equipment can be a physical piece of ophthalmic equipment or a virtual one.

The characteristics of the visual equipment may be selected among real existing equipments, or constructed as desired, as a virtual visual equipment.

The wearer may be either a real person, or a virtual being, representative of a predetermined group of users or deemed to be an average user.

The wearer may be chosen from a database of multiple wearers, in which the wearers are organized in clusters according to a particular characteristic, such as age, gender, ethnicity, activity, refraction, etc.

The expression "the wearer" means that the person or virtual being is wearing the visual equipment the performance of which is to be evaluated.

The model Ms of the scene may comprise at least one object defined by at least one geometric parameter and by a position of the object in the scene. The scene may be made of tridimensional objects in a tridimensional environment.

Other features of the scene may be included in the model Ms, including color, texture, contrast, light sources, etc.

The model Mt of the visual task may comprise a sequence of points to be looked at in the model Ms of the scene. Optionally, the time instant at which each point is looked at may be included in the model Mt of the visual task.

Additional parameters may be included in the model Mt of the visual task, such as the minimum visual acuity or the maximum visual acuity loss with which a given object point must be seen, or the time interval between one fixation point and the next one.

Said wearer (physical or virtual) and visual equipment (physical or virtual) are defined by some characteristics, which are taken into account in the model of the scene and in a model of the wearer.

Moreover, additional visual task parameters may be taken into account in the model Mt of the visual task, such as visual fatigue, attention, peripheral vision, fusion, etc.

In other words, the model Mt of the visual task may be a list of fixation points also referred to as fixations, where each fixation may be defined by its position on a given object of the scene, either in a predetermined reference frame of the object, or in a predetermined "main" reference frame in the scene, with optionally the minimum visual acuity or maximum visual acuity loss for the fixation, also optionally, the duration of the fixation and also optionally, any other visual task parameters.

A first non-limiting example of a visual task is as follows. A computer screen is placed in front of the wearer, at a distance of 70 cm. A grid of points is defined which covers the screen and which represents the position of the saccades when a wearer is reading a text on the computer screen. The visual task consists in looking at each point of the grid, sequentially, from top left to bottom right, with an acuity loss lower than or equal to 0.1 log MAR (with reference to the Logarithm of the Minimum Angle of Resolution) at each point.

A second non-limiting example of a visual task may be as follows. A television screen is placed in front of the wearer, at a distance of 3 m. A random set of points is defined on the screen, which represent the positions of the fixation points when a wearer is watching a movie. The visual task consists in looking at each point of the set of points, sequentially, in a random order, with an acuity loss lower than or equal to 0.2 log MAR.

Figure 2:
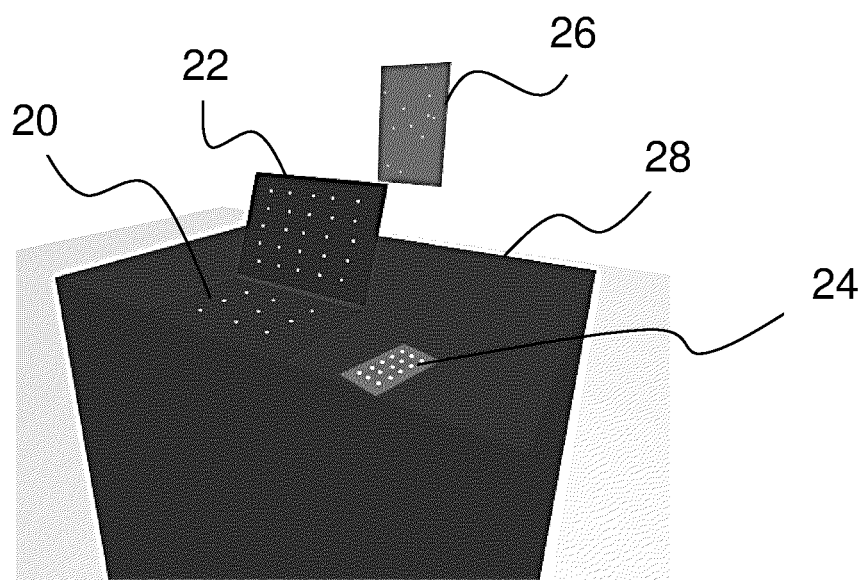
FIG. 2 is a schematic view of an example of a model of a scene obtained by a device according to the invention, in a particular embodiment.

FIG. 2 gives a non-limiting example of a model of a scene including a laptop keyboard 20, a laptop screen 22, a smartphone 24 and a person 26 standing in front of the wearer. The smartphone 24 and the laptop, comprising the laptop keyboard 20 and the laptop screen 22, are located on a desk 28. The points to be looked at in the scene are defined and shown in FIG. 2 on the laptop keyboard 20, the laptop screen 22, the smartphone 24 and the person 26. In this example, the visual task consists in looking sequentially at each point defined in the scene in a predefined order.

More generally, the model Ms of the scene may comprise a main reference frame, which is the general reference frame of the environment considered in the scene. The model Ms of the scene may further comprise one or more objects, each object having its own reference frame. The shape of an object may comprise geometric forms defined in the reference frame of the object, such as points, lines, rectangles, spheres, parallelepipeds, triangular meshes and/or quad meshes. The position of an object in the scene may be defined with respect to the main reference frame.

For example, the position of an object with respect to the main reference frame may be described by using a rotation matrix R and a translation matrix T. For example, the rotation matrix R is a 3×3 matrix and the translation matrix T is a 3×1 vector.

The coordinates of a given point in the reference frame of an object are given by a triplet Po and the coordinates of that point in the main reference frame are given by a triplet Pm.

The transformation from the main reference frame to the reference frame of the object is given by (R, T) such that Po=R×Pm+T.

Each object may thus be defined by its geometry and the transformation (R, T).

The wearer may be modeled as a set of rigid body parts capable of moving with respect to each other.

Figure 3:
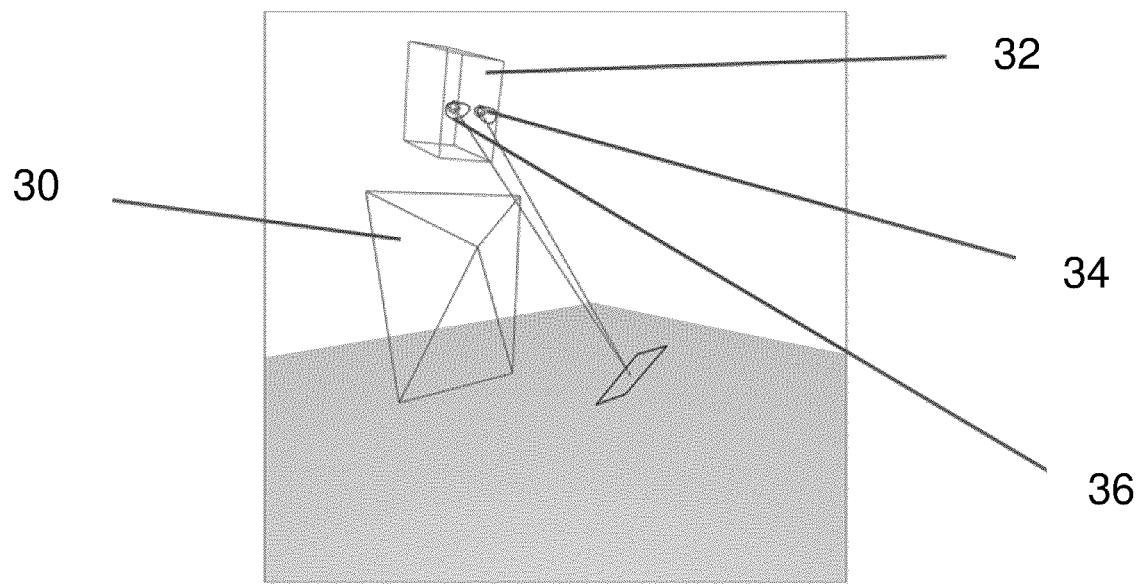
FIG. 3 is a schematic view of an example of a model of a wearer obtained by a device according to the invention, in a particular embodiment.

As shown in FIG. 3, the model Mw of the wearer comprises a head 32 movable with respect to the model Ms of the scene and at least one eye 34 rotationally movable with respect to the head 32. The at least one eye 34 is a means for the head 32 for looking at a given point without being bound to the rotation of the head 32. At least one ophthalmic and/or solar lens 36 pertaining to the visual equipment cooperates with the eye in front of which it is positioned.

Optionally, the model Mw of the wearer may also comprise a trunk or torso 30 movable with respect to the model Ms of the scene, the head 32 being rotationally movable with respect to the trunk 30.

The trunk 30 may be considered as static in the main reference frame of the scene for the duration of the visual task.

As a variant, the model Mw of the wearer may comprise a predetermined motion of the trunk 30. For example, the motion of the trunk 30 may be a typical trunk motion that has been previously recorded, such as the motion of the trunk during a given activity: walking, running, climbing stairs, etc. In addition, optionally, an effort of the wearer to move the trunk with respect to the waist may be taken into account in the wearer model Mw.

Optionally, the model Mw of the wearer may further comprise other parameters relating to the wearer, such as data relating to the size of the wearer and/or the manner in which the wearer is moving and/or a particular type of visual deficiency of the wearer, e.g. myopia or hypermetropia, etc.

Regarding the motion of the head 32, several models of head motions are known, for example from the article by M. Kunin, Y. Osaki, B. Cohen and T. Raphan entitled "Rotation Axes of the Head During Positioning, Head Shaking, and Locomotion", in J. Neurophysiol. 98, pages 3095-3108, 2007.

The reference frame of the trunk may be defined as follows. The origin of the trunk reference frame is located at the midpoint between the left shoulder point and the right shoulder point. The X-axis of the trunk reference frame passes through the shoulder points and points toward the right side of the wearer in a direction corresponding to the horizontal direction. The Z-axis points toward the back of the wearer in the horizontal direction and is perpendicular to the line joining the two shoulder points. The Y-axis points upwards, in a direction corresponding to the vertical direction and is orthogonal to the X-axis and to the Z-axis.

The reference frame of the head may be defined as follows. The origin of the head reference frame is located at the midpoint between the two tragions. The X-axis of the head reference frame passes through the two tragions and points toward the right side of the wearer in a direction corresponding to the horizontal direction. The Z-axis of the head reference frame point toward the back of the wearer in the horizontal direction and is perpendicular to the line joining the two tragions. The Y-axis points upwards, in a direction corresponding to the vertical direction and is orthogonal to the X-axis and to the Z-axis.

For example, the head motion may be described by three angles theta, phi and rho, corresponding respectively to head pitch, yaw and roll. For example, the transformation matrix from the reference frame of the trunk to the reference frame of the head may be the combination of a rotation about an X-axis of an angle equal to k×theta, a translation about an Y-axis, orthogonal to the X-axis, of a distance equal to the trunk to head distance, a rotation about a Z-axis, orthogonal to the X-axis and to the Y-axis, of an angle equal to rho, a rotation about the X-axis of an angle equal to (1−k)×theta and a rotation about the Y-axis of an angle equal to phi, where k=0.22.

The eye motions may for example be described by two angles corresponding to eye gaze directions: lowering and azimuth. Optionally, the torsion of the eye may also be taken into account. For example, the eye motions may be described according to Listing's law.

The lens or lenses may be defined by their geometry i.e. shape, material or refractive index, and position with respect to the eye(s) and/or head of the wearer.

As shown in FIG. 1, the device 10 also comprises at least one processor 14.

According to the invention, the processor 14 is configured for determining at least one head posture HP for respectively at least one of the fixation points so that the model Mw of the wearer looks respectively at the at least one of the fixation points.

For a given fixation point Pi belonging to the task model Mt, the head posture can be determined as follows:
1) Set the head of the wearer model Mw in its upright position.
2) Compute the position (xi, yi, zi) of the fixation point Pi in the head reference frame.
3) From the cartesian coordinates (xi, yi, zi), compute the elevation and azimuth (theta_i, phi_i) of the fixation point.
4) The head rotation for the trunk can be obtained as a fraction of the elevation and azimuth of the fixation point, according to gain values (k_vertical, k_horizontal):
theta=k_vertical×theta_i
phi=k_horizontal×phi_i
rho=0

For example, one can take k_vertical=k_horizontal=0.3.

The above rough method for determining the head posture is an alternative to a more precise method that will be described later.

Optionally, the processor 14 may be further configured for determining at least one gaze direction in addition to the at least one head posture HP for respectively the at least one of the fixation points so that the model Mw of the wearer looks respectively at the at least one of the fixation points.

Once the head position is known, one can determine the gaze direction of an eye such that the gaze intersects the fixation point after refraction through the lens.

According to the invention, the processor 14 is further configured for determining at least one task-directed performance parameter PP for the wearer performing the visual task with the determined head posture HP for respectively the at least one of the fixation points. Such performance parameter determination is made on the basis of the wearer model Mw, the scene model Ms and the visual task model Mt.

By way of non-limiting examples, the task-directed performance parameter PP may be any of a head posture effort, an eye gaze effort, a task-directed visual acuity, a task-directed distortion. The task-directed distortion can pertain notably to a stereo distortion, an optical flow, a magnification and/or a vergence.

Thus, determining the task-directed performance parameter PP may comprise determining a gaze effort of the wearer and/or a posture effort of the wearer performing the visual task.

According to the invention, the processor 14 is also configured for providing the at least one task-directed performance parameter PP for determining to which extent the visual equipment is appropriate for the wearer.

For a wearer to look at a given object point through a pair of glasses, for a fixed trunk position, there are usually an infinite number of possibilities, corresponding to different head positions. For each head position, the wearer will adjust the gaze direction of the eyes to look at the given object point.

The processor 14 may be configured for determining, for respectively the at least one of the fixation points, at least one punctual physiological effort corresponding to multiple possible head postures and determining the at least one head posture for respectively the at least one of the fixation points as a function of the determined at least one punctual physiological effort.

The punctual physiological effort may for example comprise a head posture effort, which is the physiological effort made by the model Mw of the wearer for having such a head posture.

A head posture effort function may compute the effort made by the wearer to maintain a position of the head. It is a unitless function expressing the relative effort between various head positions. Typically, the posture effort is minimum for a head lowering, head azimuth and head torsion angles of zero degree. Typically, the head posture effort is maximum when the head angles are at their maximum. Typically, the head posture effort values range between zero and one. The punctual physiological effort may for example comprise, instead of the head posture effort or in addition to the head posture effort, a gaze effort of at least one eye, which is the physiological effort made by the model Mw of the wearer for having such a gaze direction.

A gaze effort function may compute, for at least one eye, the effort made by the wearer to maintain a position as a function of the gaze direction. It is a unitless function expressing the relative effort between various head positions. Typically, the gaze effort is minimum for a gaze lowering angle of about 15 degrees and a gaze azimuth angle of zero degree. Typically, the gaze effort is maximum when the gaze angle is at its maximum. Typically, the gaze effort values range between zero and one.

Determining the task-directed performance parameter PP for the wearer performing the visual task may for example comprise determining at least one punctual performance parameter for the wearer performing the visual task with respectively the at least one head posture for respectively the at least one of the fixation points and obtaining the task-directed performance parameter PP from the at least one punctual performance parameter, for example by determining an average value or a cumulated value of the punctual performance parameters.

The processor 14 may be configured for determining the at least one head posture HP for respectively at least one of the fixation points as a function of punctual deviations of visual acuity with respect to a visual acuity target, corresponding to multiple possible head postures.

Moreover, determining the task-directed performance parameter PP may comprise determining at least one of a task-directed visual acuity and a task-directed distortion (which, as described above, can pertain notably to a stereo distortion, an optical flow, a magnification and/or a vergence).

A visual acuity model may compute, for a given object point and wearer head posture, the visual acuity with which the point is seen by the wearer. This model may take into account the aberrations of the lens in the gaze direction of the wearer. It may also take into account an accommodation value of the wearer or the maximum visual acuity of the wearer. A visual acuity model such as the one described in document WO 2017/064065 A1 may be used.

An overall task-directed visual acuity may then be determined on the basis of the visual acuity associated with each fixation point.

It is to be noted that the exploitation of a task-directed visual acuity does not necessarily involve that a punctual deviation with respect to a visual acuity target is used in determining the head posture for the fixation points of the visual task. Conversely, using a punctual deviation with respect to a visual acuity target does not involve that the task-directed visual acuity is necessarily taken into account in evaluating the performance of the visual equipment.

Each of the head posture effort function, gaze effort function and visual acuity model may be any of an average model, a model built on the basis of measurements made for a given wearer, or a model for a segment or cluster of wearers having for example a common particular characteristic such as gender, age, ethnicity, activity, refraction, etc.

Measurement of head posture efforts for an individual can be assessed through a psychophysical measurement. For example, a wearer can express the perceived effort while maintaining a given head angle. By repeating this measurement for different head angles, the head posture effort function can be determined. Alternatively, the head motion range of an individual can be measured. The head posture effort can then be modelled as a quadratic function equal to zero in the resting posture and reaching one at the maximum head angle.

Similarly, gaze efforts for an individual can be assessed through a psychophysical measurement. For example, a wearer can express the perceived effort while maintaining a given gaze angle. By repeating this measurement for different gaze angles, the gaze effort function can be determined. Alternatively, the eye motion range of an individual can be measured. The gaze effort can then be modelled as a quadratic function equal to zero in the resting gaze direction and reaching one at the maximum gaze direction.

The acuity loss model for an individual can be assessed by evaluating the visual acuity of an individual in response to power and astigmatism errors, and their combinations. See for example Fauquier, C., et al. "Influence of combined power error and astigmatism on visual acuity." Vision Science and Its Applications, OSA Technical Digest Series. Washington, DC: Optical Society of America (1995): 5 151-4.

By way of non-limiting example, the gaze effort of one eye may be defined as follows: alpha is the eye's gaze lowering angle in degrees, beta is the eye's gaze azimuth angle in degrees and GazeEffort is the eye's gaze effort in arbitrary units. A value of 0 represents a minimum effort. A value of 1 represents a maximum effort. This model has been obtained through an internal study on 74 subjects.

a=alpha/100
b=beta/100

$$GazeEffort(alpha,beta)=4.7398-46.0510a+170.4699b^2+146.0116a^2+9.9626a^3+77.7729b^2a-0.7459b^4+85.2274a^4-21.3346b^2a^2$$

By way of non-limiting example, the head posture effort may be defined as follows. Referring to the above-mentioned head rotation angles theta, phi and rho, corresponding respectively to head pitch, yaw and roll, theta is the rotation angle of the head about the X-axis in degrees, phi is the rotation angle of the head about the Y-axis in degrees, rho is the rotation angle about the Z-axis in degrees, all rotations being defined with respect to the trunk, and HeadPostureEffort is the head posture effort in arbitrary units. A value of 0 represents a minimum effort. A value of 1 represents a maximum effort. The numbers 80, 80 and 45 in the formula represent respectively the maximum head rotation angles around the x, y, and z axes, in degrees. A quadratic variation of head posture effort with head angle is assumed.

$HeadPostureEffort(theta,phi,rho)=ex+ey+ez$, where:

$ex=(theta/80)^2$
$ey=(phi/80)^2$
$ez=(rho/45)^2$

A cost function associated with the model Mw of the wearer looking at a given object point with a given head posture may then be defined on the basis of the head posture effort and/or the gaze effort, possibly combined with the visual acuity, as follows.

1) For a given head posture defined by the head rotation angles (theta, phi, rho), the gaze directions of the left eye, GazeDirectionLeftEye(theta, phi, rho) and/or of the right eye GazeDirectionRightEye(theta, phi, rho) for fixation of the given object point through the lenses may be computed, for example by ray tracing, taking into account deviations by the lenses:

alpha_left,beta_left=GazeDirectionLeftEye(theta,phi,rho)

alpha_right,beta_right=GazeDirectionRightEye(theta,phi,rho)

where alpha_left is the gaze lowering angle of the left eye, beta_left is the gaze azimuth angle of the left eye, alpha_right is the gaze lowering angle of the right eye and beta_right is the gaze azimuth angle of the right eye.

2) From the gaze directions of the left and right eyes, the gaze effort for the left eye, gaze_effort_left and the gaze effort for the right eye, gaze_effort_right, may be evaluated:

gaze_effort_left=GazeEffort(alpha_left,beta_left)

gaze_effort_right=GazeEffort(alpha_right,beta_right)

3) From the head rotation angles theta, phi and rho, the head posture effort, head_posture_effort, may be evaluated:

head_posture_effort=HeadPostureEffort(theta,phi,rho)

4) Optionally, if the object point is associated with a target visual acuity value, the visual acuity with which the point is seen, acuity_value, may be evaluated:

acuity_value=AcuityModel(alpha_left,beta_left,alpha_right,beta_right)

5) If the visual acuity, acuity_value, with which the point is seen is lower than the target visual acuity, acuity_target, a visual acuity penalty, acuity_penalty, may be computed:

acuity_penalty=max(acuity_target−acuity_value,0)

where max(acuity_target−acuity_value, 0) is the highest value between 0 and the difference between the visual acuity target value and the actual visual acuity value.

Then, the cost function related to the head posture, Cost(posture), which depends on the head rotation angles theta, phi and rho, may be defined as follows:

Cost(posture)=Cost(theta,phi,rho)=gaze_effort_left+
gaze_effort_right+head_posture_effort+acuity_penalty Optionally, additional terms can be taken into account in the posture cost function.

6) By using an optimization method, the optimum head posture, defined as the head posture, given by (theta, phi, rho), that minimizes the cost function Cost(posture), can then be obtained. For example, the optimum head posture may be obtained by using a gradient descent method.
7) The head posture effort for the optimum head posture may then be computed.
8) Steps 1 to 7 above may be repeated for each fixation point in the visual task.

Using the above process, the head posture effort at each fixation point of a visual task, for a given visual equipment, may be determined.

For the entire visual task, the average head posture effort involved, the maximum and minimum head posture efforts and/or the cumulated head posture effort may be determined.

Similarly, the gaze effort required at each fixation point of a given visual task with a given visual equipment may be determined, as well as for the entire visual task, the average gaze effort, the maximum and minimum gaze efforts and/or the cumulated gaze effort.

The visual acuity of a wearer when performing a visual task may also be determined.

The above process may be used for comparing two visual equipments, in terms of their impact on posture effort or gaze effort or visual acuity.

For example, if equipment A requires less global posture and gaze efforts than equipment B to perform a given visual task, then equipment A will be considered as having a better performance than equipment B and as being more appropriate for the considered wearer.

The parameters defining the model Mw of the wearer may be average parameters.

As a variant, they may be segmented parameters, i.e. parameters of a predetermined category or cluster of wearers. As mentioned previously, non-limiting examples of such categories are gender (man or woman), age (child, or young adult, or adult, or senior), ethnicity, activity, refraction, etc.

As another variant, the parameters defining the model Mw of the wearer may be personalized i.e. they may be the parameters of an individual wearer.

The parameters that may be segmented or personalized include: the gaze effort model as a function of gaze direction and/or the head posture effort model as a function of the head posture and/or the visual acuity model as a function of lens aberrations and/or the prescription for at least one eye and/or the position of at least one eye in the head and/or the ranges of motion of at least one eye and/or the ranges of motion of the head.

Figure 4:
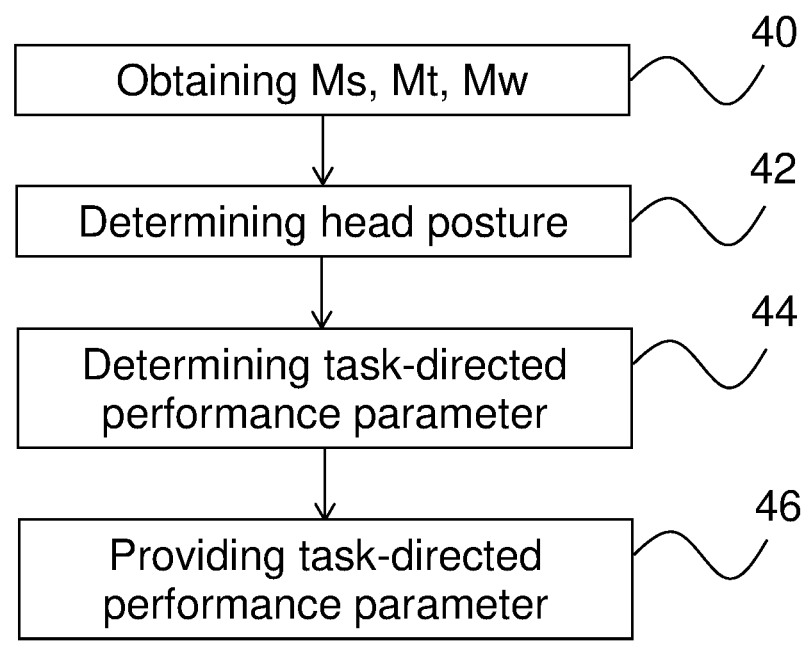
FIG. 4 is a flow diagram showing steps of a method according to the invention, in a particular embodiment.

The flow diagram of FIG. 4 shows steps of a method according to the invention for evaluating a performance of a visual equipment for at least one wearer of the visual equipment to perform at least one visual task.

A first step 40 comprises obtaining the model Ms of the scene, the model Mt of the visual task(s) and the model Mw of the wearer, as described above in relationship with the device according to the invention.

A following step 42 comprises determining, by at least one processor such as for example the processor 14, at least one head posture HP for respectively at least one of the fixation points so that the model Mw of the wearer looks respectively at the at least one of the fixation points, for example as described above in relationship with the device 10.

A following step 44 comprises determining, by at least one processor such as for example the processor 14, at least one task-directed performance parameter PP for the wearer performing the visual task(s) with the at least one head posture HP for respectively the at least one of the fixation points, on the basis of the wearer model Mw, the scene model Ms and the visual task model Mt obtained at step 40, for example as described above in relationship with the device 10.

Then, a step 46 comprises providing the task-directed performance parameter PP, for determining to which extent the visual equipment is appropriate for the wearer, for example as described above in relationship with the device 10.

In a particular embodiment, the method according to the invention is computer-implemented. Namely, a computer program product comprises one or more sequences of instructions that are accessible to a processor and that, when executed by the processor, cause the processor to carry out steps of the method for evaluating a performance of a visual equipment for at least one wearer of that visual equipment to perform at least one visual task as described above.

The models of the scene Ms, of the visual task Mt and of the wearer Mw may be built for example remotely in a cloud, or locally in a computer.

The sequence(s) of instructions may be stored in one or several computer-readable storage medium/media, including a predetermined location in a cloud.

An example is described below where the performances of two different pairs of ophthalmic lenses are compared by using the device or method according to the disclosure.

Figure 5:
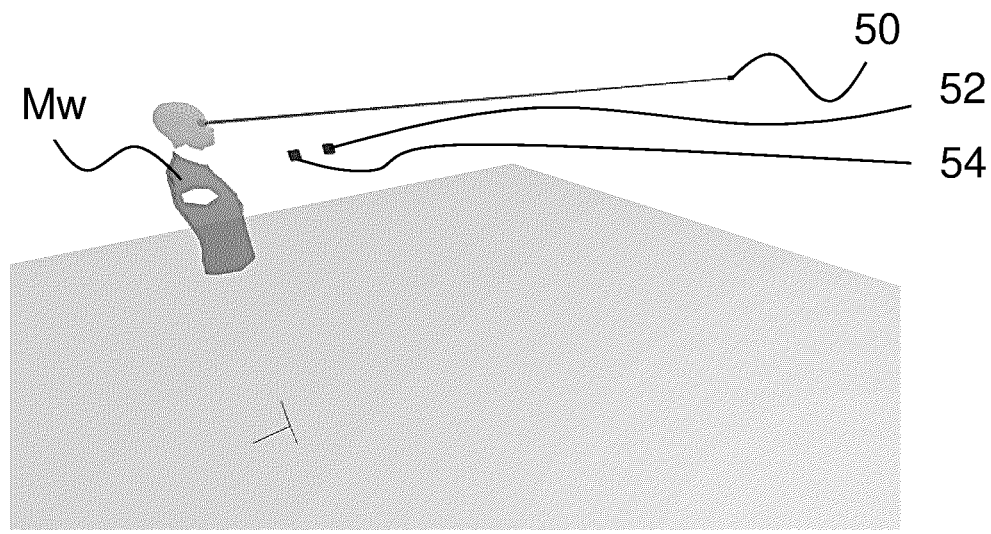
FIG. 5 is a schematic view of an example of a modeled wearer performing a modeled visual task in a modeled scene according to the present invention.

As shown in FIG. 5, the modeled visual task is a task of visual transition between a far vision point 50 and an intermediate vision point 52 and then a near vision point 54.

The task of looking at the far vision point 50 is materialized on FIG. 5 by a solid straight line from the wearer's head to the far vision point 50.

There is no object in the scene. All fixation points are defined in the main reference frame, as follows. All distances are in millimeters.

The far vision point 50 is located at position (x=0, y=1820, z=−5000). The intermediate vision point 52 is located at position (x=0, y=1630, z=−590). The near vision point is located at position (x=0, y=1620, z=−416).

For each point, the maximum visual acuity loss is 0.1 log MAR. The fixation duration is 0.5 s.

As regards the model Mw of the wearer, the following parameters are taken into account.

The wearer prescription is sphere=+2, cylinder=0, axe=0, addition=2 for the left and right eyes.

The half-pupillary distance is 32.5 mm for the left and right eyes.

The trunk of the wearer is located at position (x=0, y=1600, z=0) in the main reference frame.

The head of the wearer is located at position (x=0, y=200, z=0) in the trunk reference frame.

The center of rotation of the left eye is located at position (x=−32.5, y=20, z=−70) in the head reference frame.

The center of rotation of the right eye is located at position (x=32.5, y=20, z=−70) in the head reference frame.

The wearer is equipped with a pair of progressive lenses. The positioning parameters are: center of rotation of the eye to lens distance=25.5 mm, pantoscopic tilt=−8 degrees and wrap angle=0 degree.

The first pair of lenses has lenses with a progression length of 17 mm.

The second pair of lenses has lenses with a progression length of 14 mm.

Figure 6:
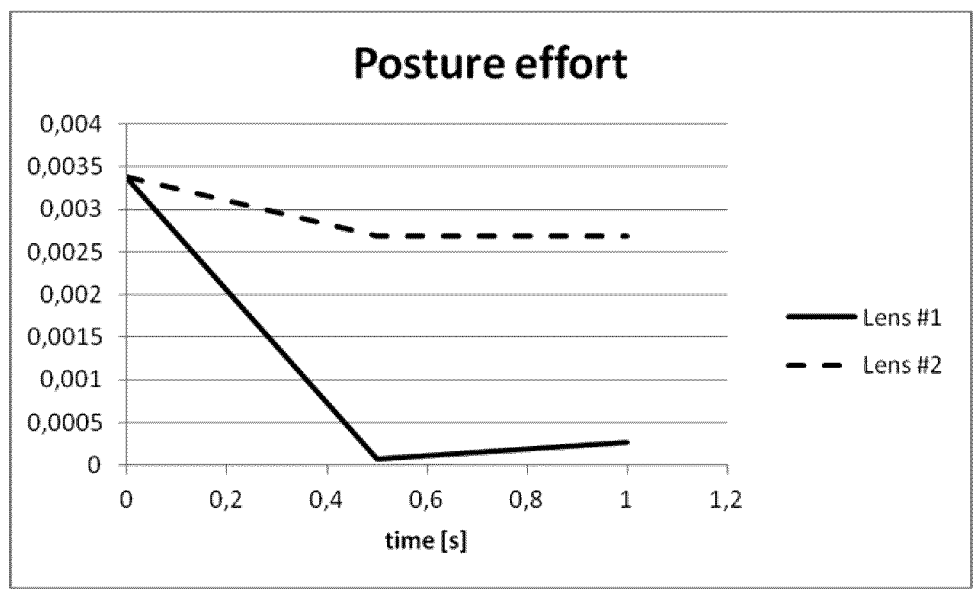
FIG. 6 is a graph showing a simulation of a head posture effort of a wearer performing the visual task shown in FIG. 5 when wearing two different pairs of lenses, such simulation being obtained by a device or method according to the invention.

The two curves shown in FIG. 6 illustrate the computed head posture effort (in arbitrary units) as a function of time (in seconds), made by the model Mw of the wearer when wearing the first pair of lenses (solid line) and the second pair of lenses (dashed line) and performing the visual task of FIG. 5.

Figure 7:
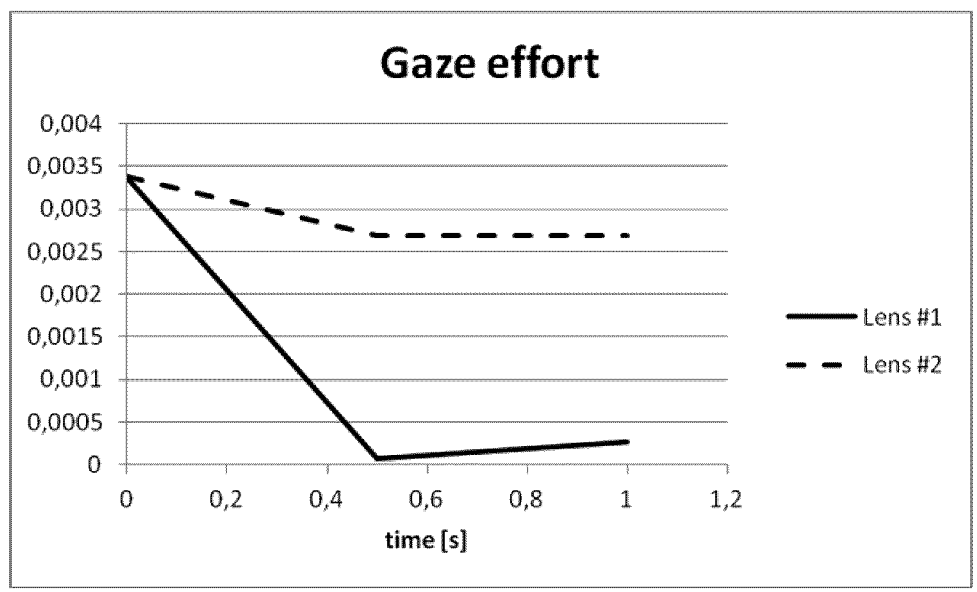
FIG. 7 is a graph showing a simulation of a gaze effort of a wearer performing the visual task shown in FIG. 5 when wearing two different pairs of lenses, such simulation being obtained by a device or method according to the invention.

The two curves shown in FIG. 7 illustrate the computed gaze effort (in arbitrary units) as a function of time (in seconds), made by the model Mw of the wearer when wearing the first pair of lenses (solid line) and the second pair of lenses (dashed line) and performing the visual task of FIG. 5.

It can be seen that both pairs of lenses require the same head posture and gaze effort for looking at the far vision point 50, at time instant t=0.

The second pair of lenses requires more head posture and gaze efforts than the first pair of lenses for looking at the intermediate vision point 52 and at the near vision point 54. The reason is that the progression length is shorter for the second pair of lenses than for the first pair of lenses. The required head lowering and gaze lowering angles are therefore smaller for the second pair of lenses than for the first pair of lenses.

As a conclusion, in this example, the first pair of lenses is more appropriate than the second pair of lenses for the considered wearer.

Such simulations of the performances of a given lens design may be useful for example for a lens designer, for comparing the performances of various lens designs or for personalizing a lens for a given wearer.

Although representative methods and devices have been described in detail herein, those skilled in the art will recognize that various substitutions and modifications may be made without departing from the scope of what is described and defined by the appended claims.

The invention claimed is:

1. A device for evaluating a performance of a visual equipment for at least one wearer of said visual equipment to perform at least one visual task, comprising:
at least one input adapted to:
obtain a model of a scene where said at least one visual task is performed;
obtain a model of said at least one visual task, the model of said at least one visual task comprising a sequence of points to be looked at in the model of the scene; and
obtain a model of said wearer, the model of the wearer comprising a head movable with respect to the model of the scene and at least one eye rotationally movable with respect to the head, said visual equipment cooperating with said at least one eye;
at least one processor configured for:
determining at least one head posture for respectively at least one of said points so that the model of the wearer looks respectively at said at least one of said points;
determining at least one task-directed performance parameter for said wearer performing said at least one visual task with said at least one head posture for respectively said at least one of said points, on the basis of said wearer model, said scene model and said visual task model; and
providing said at least one task-directed performance parameter for determining to which extent said visual equipment is appropriate for said wearer.

2. The device according to claim 1, wherein said at least one processor is further configured for:
determining at least one punctual performance parameter for said wearer performing said at least one visual task with respectively said at least one head posture for respectively said at least one of said points;
obtaining said at least one task-directed performance parameter from said at least one punctual performance parameter.

3. The device according to claim 2, wherein said at least one processor is configured for determining at least one gaze direction in addition to said at least one head posture for respectively said at least one of said points so that the model of the wearer looks respectively at said at least one of said points.

4. The device according to claim 2, wherein said determining said task-directed performance parameter comprises determining a gaze effort.

5. The device according to claim 2, wherein said determining said task-directed performance parameter comprises determining a head posture effort.

6. The device according to claim 1, wherein said at least one processor is configured for determining at least one gaze direction in addition to said at least one head posture for respectively said at least one of said points so that the model of the wearer looks respectively at said at least one of said points.

7. The device according to claim 6, wherein said determining said task-directed performance parameter comprises determining a gaze effort.

8. The device according to claim 6, wherein said determining said task-directed performance parameter comprises determining a head posture effort.

9. The device according to claim 1, wherein said determining said task-directed performance parameter comprises determining a gaze effort.

10. The device according to claim 1, wherein said determining said task-directed performance parameter comprises determining a head posture effort.

11. The device according to claim 1, wherein said model of said scene comprises at least one object defined by at least one geometric parameter and by a position of said at least one object in said scene.

12. The device according to claim 1, wherein said model of said wearer further comprises a trunk movable with respect to the model of the scene, the head being rotationally movable with respect to said trunk.

13. The device according to claim 1, wherein said at least one processor is configured for determining for respectively said at least one of said points at least one punctual physiological effort corresponding to multiple possible head postures and determining said at least one head posture for respectively said at least one of said points as a function of said determined at least one punctual physiological effort.

14. The device according to claim 13, wherein said punctual physiological effort comprises a head posture effort.

15. The device according to claim 13, wherein said punctual physiological effort comprises a gaze effort of at least one eye.

16. The device according to claim 13, wherein said at least one processor is configured for determining said at least one head posture for respectively said at least one of said points as a function of punctual deviations of visual acuity with respect to a visual acuity target corresponding to multiple possible head postures.

17. The device according to claim 1, wherein said model of said wearer comprises at least one personalized parameter pertaining to a group including: a gaze effort model as a function of a gaze direction; a head posture effort model as a function of a head posture; a visual acuity model as a function of lens aberrations; a prescription for said at least one eye; a position of said at least one eye in said head; ranges of motion of said at least one eye; ranges of motion of said head.

18. The device according to claim 1, wherein determining said task-directed performance parameter comprises determining at least one of a task-directed visual acuity and a task-directed distortion.

19. A method for evaluating a performance of a visual equipment for at least one wearer of said visual equipment to perform at least one visual task, the method comprising:
obtaining a model of a scene where said at least one visual task is performed;
obtaining a model of said at least one visual task, the model of said at least one visual task comprising a sequence of points to be looked at in the model of the scene;
obtaining a model of said wearer, the model of the wearer comprising a head movable with respect to the model of the scene and at least one eye rotationally movable with respect to the head, said visual equipment cooperating with said at least one eye;
determining by at least one processor at least one head posture for respectively at least one of said points so that the model of the wearer looks respectively at said at least one of said points;
determining by at least one processor at least one task-directed performance parameter for said wearer performing said at least one visual task with said at least one head posture for respectively said at least one of said points, on the basis of said wearer model, said scene model and said visual task model; and
providing said at least one task-directed performance parameter for determining to which extent said visual equipment is appropriate for said wearer.

20. A non-transitory computer-readable medium on which is stored a computer program for evaluating a performance of a visual equipment for at least one wearer of said visual equipment to perform at least one visual task, the computer program comprising one or more sequences of instructions that are accessible to a processor and that, when executed by said processor, cause said processor to:
obtain a model of a scene where said at least one visual task is performed;
obtain a model of said at least one visual task, the model of said at least one visual task comprising a sequence of points to be looked at in the model of the scene;
obtain a model of said wearer, the model of the wearer comprising a head movable with respect to the model of the scene and at least one eye rotationally movable with respect to the head, said visual equipment cooperating with said at least one eye;
determine at least one head posture for respectively at least one of said points so that the model of the wearer looks respectively at said at least one of said points;
determine at least one task-directed performance parameter for said wearer performing said at least one visual task with said at least one head posture for respectively said at least one of said points, on the basis of said wearer model, said scene model and said visual task model; and
provide said at least one task-directed performance parameter for determining to which extent said visual equipment is appropriate for said wearer.

* * * * *